United States Patent
Indo et al.

(10) Patent No.: US 9,546,959 B2
(45) Date of Patent: Jan. 17, 2017

(54) METHOD AND SYSTEM FOR MEASUREMENT OF RESERVOIR FLUID PROPERTIES

(75) Inventors: Kentaro Indo, Sugar Land, TX (US); Michael M. Toribio, Toronto (CA); Shu Pan, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 708 days.

(21) Appl. No.: 13/234,621

(22) Filed: Sep. 16, 2011

(65) Prior Publication Data

US 2013/0071934 A1    Mar. 21, 2013

(51) Int. Cl.
| | |
|---|---|
| *G01N 21/80* | (2006.01) |
| *G01N 33/28* | (2006.01) |
| *E21B 49/10* | (2006.01) |
| *G01N 21/00* | (2006.01) |
| *E21B 49/08* | (2006.01) |

(52) U.S. Cl.
CPC .............. *G01N 21/80* (2013.01); *E21B 49/10* (2013.01); *G01N 33/287* (2013.01); *E21B 2049/085* (2013.01)

(58) Field of Classification Search
CPC .. G01N 21/80; G01N 33/2841; G01N 33/287; E21B 2049/085; E21B 49/10
USPC ........................................ 436/28; 422/82.05
See application file for complete search history.

(56) References Cited

U.S. PATENT DOCUMENTS

| | | | |
|---|---|---|---|
| 6,939,717 B2 | 9/2005 | Jiang et al. | |
| 7,025,138 B2 * | 4/2006 | Kurkjian et al. | 166/250.05 |
| 7,339,160 B2 | 3/2008 | Raghuraman et al. | |
| 7,427,504 B2 | 9/2008 | Torgersen et al. | |
| 7,432,109 B2 | 10/2008 | Raghuraman et al. | |

(Continued)

FOREIGN PATENT DOCUMENTS

| | | |
|---|---|---|
| GB | 2397651 A | 7/2004 |
| WO | 0163094 A1 | 8/2001 |
| WO | 2007034131 A1 | 3/2007 |

OTHER PUBLICATIONS

Anonymous, "Quantitative fluid measurements at reservoir conditions, in real time," InSitu Fluid Analyzer Brochure, 2008, Schlumberger: pp. 1-8, <www.sib.com/insitu>.

(Continued)

*Primary Examiner* — Rebecca M Fritchman
(74) *Attorney, Agent, or Firm* — Michael Dae

(57) ABSTRACT

A method and system that characterizes hydrogen sulfide in petroleum fluid employs a tool that includes a fluid analyzer for performing fluid analysis (including optical density (OD) for measuring carbon dioxide concentration) of a live oil sample, and a storage chamber for an analytical reagent fluidly coupled to a measurement chamber. An emulsion from fluid of the sample and the reagent is produced into the measurement chamber. The reagent changes color due to pH changes arising from chemical reactions between components of the sample and the reagent in the measurement chamber. The tool includes an optical sensor system that measures OD of a water phase of the emulsion at one or more determined wavelengths. The pH of the water phase is derived from such OD measurements. The pH of the water phase and the carbon dioxide concentration in the sample is used to calculate hydrogen sulfide concentration in the sample.

13 Claims, 8 Drawing Sheets

(56) References Cited

U.S. PATENT DOCUMENTS

| | | |
|---|---|---|
| 8,606,531 B2 * | 12/2013 | Pinguet et al. ................. 702/24 |
| 2008/0259335 A1 | 10/2008 | Raghuraman et al. |
| 2009/0047181 A1 | 2/2009 | Torgersen et al. |
| 2009/0084175 A1 | 4/2009 | Raghuraman et al. |
| 2009/0107667 A1 | 4/2009 | Mullins et al. |
| 2012/0059636 A1 * | 3/2012 | Roy et al. ......................... 703/2 |

OTHER PUBLICATIONS

Patil et al., "Predication of CO2 and H2S Solubility in Aqueous MDEA Solutions Using an Extended Kent and Eisenberg Model," IChemE, 2006, Symposium Series No. 152: pp. 498-510.

* cited by examiner

METHOD AND SYSTEM FOR MEASUREMENT OF RESERVOIR FLUID PROPERTIES

BACKGROUND

Field

The present invention relates to measurement of the properties of reservoir fluids. More specifically, the present invention is related to downhole spectroscopic measurement of reservoir fluids using oil-water mixtures.

Description of Related Art

Hydrogen sulfide ($H_2S$) can be present in subsurface hydrocarbon reservoirs. The presence of hydrogen sulfide is highly corrosive to casing, tubing, and other metallic and polymeric tools. This effect is considerably accelerated by low pH and the presence of carbon dioxide. Additionally, hydrogen sulfide is hazardous to humans even at small concentrations (for example, above 100 ppm). Thus, the measurement of the concentration of hydrogen sulfide in reservoir fluids has great value for oilfield companies because it can improve investment decisions and reduce potential health and safety hazards. For example, with knowledge of the concentration of hydrogen sulfide in the reservoir fluids, appropriate health and safety measures can be planned for the various stages of reservoir characterization and development (i.e., exploration, appraisal, development, production, and abandonment). In another example, special metals or process designs can be used that address the hydrogen sulfide concentration in the reservoir fluids. In yet another example, water or steam injection of a reservoir can promote the activity of bacteria that leads to the formation of hydrogen sulfide gas. The onset of such hydrogen sulfide formation conditions can be detected and mitigated.

At present, the measurement of the concentration of hydrogen sulfide in reservoir fluids is attained through analyzing samples captured through downhole fluid sampling tools (such as the Modular Dynamics Tester (MDT™) tool available from Schlumberger Technology Corporation of Sugar Land, Tex., USA). Such tools are typically capable of collecting samples in metal containers and maintaining them at reservoir pressure and temperature conditions. These samples are transported to a surface laboratory for fluid analysis typically involving spectroscopic and gas chromatographic analysis. Although the above technique is effective, the accuracy is somewhat compromised as it does not account for any scavenging that may take place on the metal surfaces of the sampling tool as well as any mud filtrate present in the sample container.

U.S. Pat. No. 7,025,138 discloses the use of metal coupons as a means of monitoring concentrations of hydrogen sulfide. The coupons are integrated into sampling tools and are exposed to downhole fluids. A reaction of a respective coupon with the downhole fluids causes a change in the coupon (such as a change in coloration) in the event that the concentration of hydrogen sulfide in the downhole fluid exceeds a predetermined threshold level. This technique is rather qualitative in nature in that it identifies the presence of hydrogen sulfide at a concentration over the threshold level, but does not provide a measure of the actual concentration of hydrogen sulfide. Moreover, the technique employs a reaction time in the range of two to six hours, and thus is not capable of hydrogen sulfide gas monitoring at different depths and sampling points during one trip within a wellbore.

U.S. Pat. No. 6,939,717 discloses several embodiments for the measurement of hydrogen sulfide in wellbore fluids. The first technique is based on a headspace measurement of hydrogen sulfide in the gas phase above the liquid sample, which is formed by reducing its hydrostatic pressure. The concentration of hydrogen sulfide in the original liquid hydrocarbon sample can be calculated from the measured gas phase concentration and knowledge of the Henry's law constant for the hydrocarbon sample. This measurement method can also be applied to the hydrogen sulfide content of formation water samples if the pH of the sample is either measured or fixed by a suitable buffer. The second technique is based on the measurement of the flux of hydrogen sulfide across a gas extraction membrane in contact with a flowing sample of reservoir fluid. Several methods are described to measure the flux of hydrogen sulfide across the extraction membrane. The first method uses a reduction-oxidation cell that oxidizes the hydrogen sulfide by converting ferricyanide to ferrocyanide ions and the measured reduction-oxidation current is directly proportional to the concentration of hydrogen sulphide in the reservoir fluid. The second method measures the methylene blue formed in an optical absorption cell by the reaction of the hydrogen sulfide diffused across the membrane with iron (III) ions and N,N-dimethyl-p-phenylenediamine in an acidic aqueous solution; the methylene formed is detected spectrophotometrically at a wavelength of 660 nm. The rate of change of absorbance at 660 nm is directly proportional to the concentration of hydrogen sulfide in the reservoir fluid sample. The effectiveness of the techniques of U.S. Pat. No. 6,939,717 are limited in harsh downhole conditions (for example, high pressure conditions (up to 15,000 psi) and high temperature conditions (up to 150° C.)) because the buffer compounds as well as reduction-oxidation compounds can destabilize and undergo side reactions at elevated temperatures.

International Patent Application Publication WO 2007/034131 employs an electrochemical sensor for measuring pH and hydrogen sulfide content of reservoir fluids, which in turn can be used for predicting mineral scale and for corrosion assessments. The sensor is applicable to downhole sampling tools. The effectiveness of this electrochemical sensor can be limited in harsh downhole conditions (for example, high pressure conditions (up to 15,000 psi) and high temperature conditions (up to 150° C.)) due to degradation of the sensor solution at elevated temperatures. Moreover, as the technique requires a porous membrane material to facilitate transfer of sulfide species into the aqueous mediator solution, the mechanical robustness and overall suitability for downhole deployment are limited.

A more recent study entitled "Accurate Measurement of the Hydrogen Sulfide Content in Formation Fluid Samples," SPE 94707, 2005, reports successful detection and monitoring of hydrogen sulfide concentration through a systematic sampling analysis that involved the use of an optimized and modified formation tester (i.e. minimal hydrogen sulfide scavenging) and rapid analysis on the surface to drastically reduce any incident that can contribute to underestimating hydrogen sulfide levels. This technique requires testing times on the order of days to measure hydrogen sulfide concentration, and thus is not suitable for hydrogen sulfide gas monitoring at different depths and sampling points during one trip within a wellbore.

BRIEF SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The present invention provides a downhole (in situ) sensing method and apparatus that measures the concentration of hydrogen sulfide in reservoir fluids.

A method (and corresponding apparatus) that characterizes the concentration of hydrogen sulfide in petroleum fluid employs a downhole tool that includes a fluid analyzer for performing downhole fluid analysis of a live oil sample (including optical density (OD) for measuring carbon dioxide concentration), and a storage chamber for an analytical reagent fluidly coupled to a measurement chamber. An oil-water emulsion from fluid of the live oil sample and the analytical reagent is produced in the measurement chamber. The analytical reagent changes color due to pH changes arising from chemical reactions between components of the live oil sample and the analytical reagent in the measurement chamber. The downhole tool includes an optical sensor system that measures the OD of a water phase of the oil-water emulsion at one or more determined wavelengths. The pH of the water phase is derived from such OD measurements. The pH of the water phase and the carbon dioxide concentration in the live oil sample are used to calculate hydrogen sulfide concentration in the live oil sample.

The downhole sensing method and apparatus of the present invention do not require transportation of reservoir fluids to a surface laboratory for measuring hydrogen sulfide concentration, and thus can be carried out by a downhole fluid analysis tool at multiple measurement stations during one trip of the tool within the wellbore. The present invention can also be integrated into stationary wellbore sensors in order to monitor the concentration of hydrogen sulfide in reservoir fluids.

In one embodiment, a thermodynamic model is used to calculate concentration of hydrogen sulfide in the water phase of the emulsion. The thermodynamic model relates the pH of the water phase to the concentrations of carbon dioxide components (ions) and hydrogen sulfide components (ions) that are dissolved in the water phase. The contribution of the dissolved carbon dioxide components (ions) to the pH of the water phase is derived from the measured concentration of the carbon dioxide in the live oil sample. The thermodynamic model may utilize equilibrium constants to calculate the contribution of both carbon dioxide and hydrogen sulfide to the ion concentration in the water phase, wherein the equilibrium constants are defined as function of temperature. Moreover, the concentration of hydrogen sulfide in the live oil sample may be derived from the partial pressure of hydrogen sulfide in the oil phase and the total pressure of the oil phase. Partial pressure of hydrogen sulfide in the oil phase can be calculated from the concentration of hydrogen sulfide in the water phase and Henry's constant for hydrogen sulfide.

DETAILED DESCRIPTION

Figure 1:
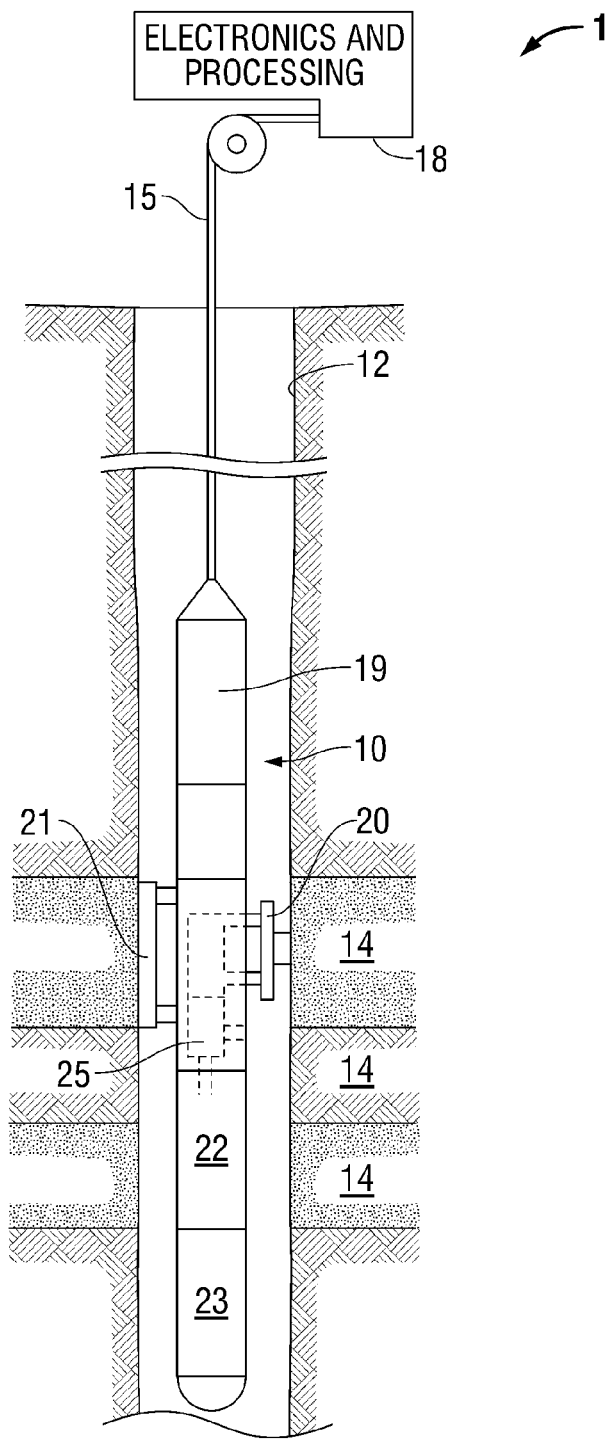
FIG. 1 is a schematic diagram of a petroleum reservoir analysis system.

FIG. 1 illustrates a petroleum reservoir analysis system 1. The system 1 includes a borehole tool 10 suspended in the borehole 12 from the lower end of a typical multiconductor cable 15 that is spooled in a usual fashion on a suitable winch on the formation surface. The cable 15 is electrically coupled to an electrical control system 18 on the formation surface. The borehole tool 10 includes an elongated body 19 which carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that fluid communication with the adjacent earth formation 14 is established. The fluid admitting assembly 20 and borehole tool 10 include a flowline leading to a fluid analysis module 25. The formation fluid obtained by the fluid admitting assembly 20 flows through the flowline and through the fluid analysis module 25. The fluid may thereafter be expelled through a port or it may be sent to one or more fluid collecting chambers 22 and 23 which may receive and retain the fluids obtained from the formation. With the fluid admitting assembly 20 sealingly engaging the earth formation 14, a short rapid pressure drop can be used to break the mudcake seal. Normally, the first fluid drawn into the borehole tool 10 will be highly contaminated with mud filtrate. As the borehole tool 10 continues to draw fluid from the formation 14, the area near the fluid admitting assembly 20 cleans up and reservoir fluid becomes the dominant constituent. The time required for cleanup depends upon many parameters, including formation permeability, fluid viscosity, the pressure differences between the borehole and the formation, and overbalanced pressure difference and its duration during drilling. Increasing the pump rate can shorten the cleanup time, but the rate should be controlled carefully to preserve formation pressure conditions.

The fluid analysis module 25 includes means for measuring the temperature and pressure of the fluid in the flowline. The fluid analysis module 25 derives properties that characterize the formation fluid sample at the flowline pressure and temperature. In one embodiment, the fluid analysis module 25 also measures absorption spectra and translates such measurements into pH of the fluid sample as well as concentrations of several components and component groups in the fluid sample. In one embodiment, the fluid analysis module 25 provides measurements of the concentrations (e.g., mole fractions, mass fractions, or weight percentages) of carbon dioxide ($CO_2$), methane ($CH_4$), ethane ($C_2H_6$), the C3-C5 alkane group, the lump of hexane and heavier alkane components (C6+), and asphaltenes. The C3-C5 alkane group includes propane, butane, and pentane. The C6+ alkane group includes hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)— also referred to as endecane or undecane, dodecane ($C_{12}H_{26}$), tridecane ($C_{13}H_{28}$), tetradecane ($C_{14}H_{30}$), pentadecane ($C_{15}H_{32}$), hexadecane ($C_{16}H_{34}$), etc. The fluid analysis module 25 also provides a means that measures live fluid density at the flowline temperature and pressure, live fluid viscosity at flowline temperature and pressure (in cP), formation pressure, and formation temperature. The fluid analysis module 25 can also include a resistivity sensor that measures resistivity of fluid in the flowline.

Control of the fluid admitting assembly 20 and fluid analysis module 25, and the flow path to the collecting chambers 22, 23 is maintained by the control system 18. As will be appreciated by those skilled in the art, the fluid analysis module 25 and the surface-located electrical control system 18 include data processing functionality (e.g., one or more microprocessors, associated memory, and other hardware and/or software) to implement the invention as described herein. The electrical control system 18 can also be realized by a distributed data processing system wherein data measured by the borehole tool 10 is communicated (potentially in real time) over a communication link (possibly a satellite link) to a remote location for data analysis as described herein. The data analysis can be carried out on a workstation or other suitable data processing system (such as a computer cluster or computing grid).

Formation fluids sampled by the borehole tool 10 may be contaminated with mud filtrate. That is, the formation fluids may be contaminated with the filtrate of a drilling fluid that seeps into the formation 14 during the drilling process. Thus, when fluids are withdrawn from the formation 14 by the fluid admitting assembly 20 they may include mud filtrate. In some examples, formation fluids are withdrawn from the formation 14 and pumped into the borehole 12 or into a large waste chamber in the borehole tool 10 until the fluid being withdrawn becomes sufficiently clean. A clean sample is one where the concentration of mud filtrate in the sample fluid is acceptably low so that the fluid substantially represents native (i.e., naturally occurring) formation fluids. In the illustrated example, the borehole tool 10 is provided with fluid collecting chambers 22 and 23 to store collected fluid samples.

The system of FIG. 1 is adapted to make in situ determinations regarding hydrocarbon-bearing geological formations by downhole sampling of reservoir fluid at one or more measurement stations within the borehole 12, and conducting downhole fluid analysis of one or more reservoir fluid samples for each measurement station. The downhole fluid analysis includes compositional analysis that estimates concentrations of a plurality of compositional components (including carbon dioxide and hydrogen sulfide) of a given sample, as well as other fluid properties.

Figure 2:
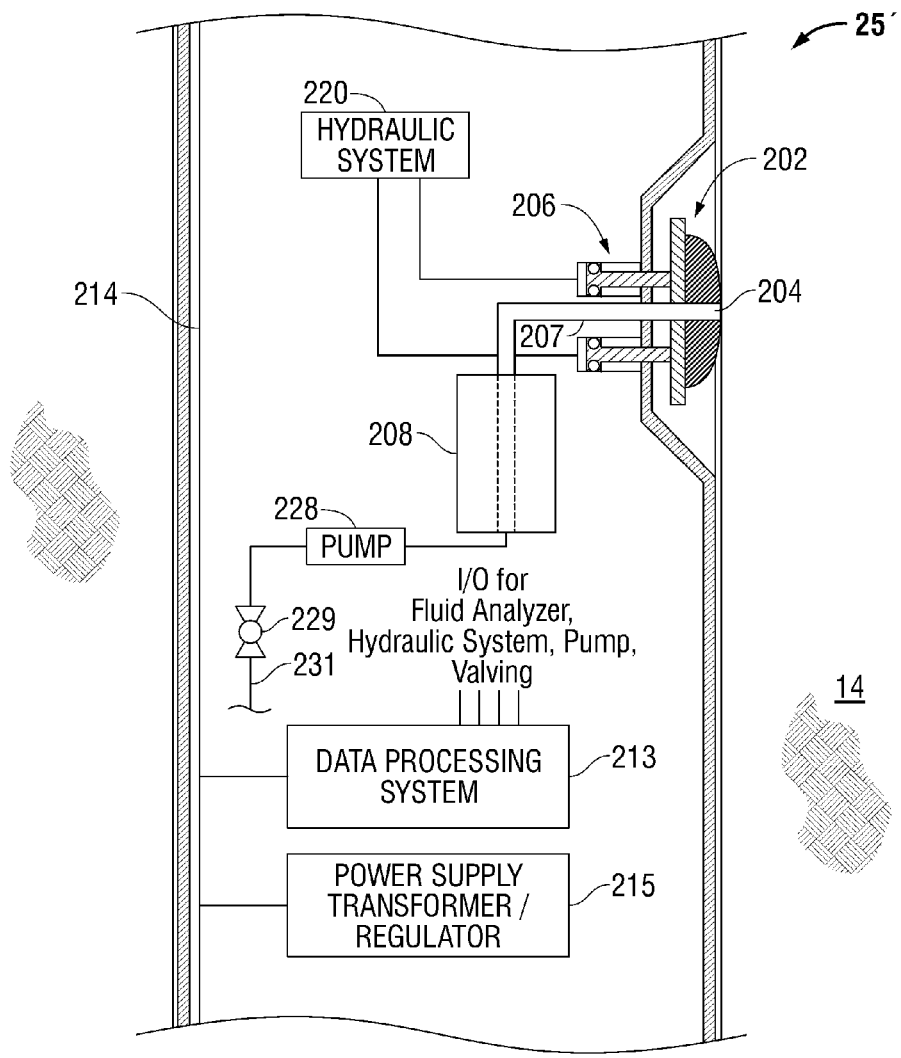
FIG. 2 is a schematic diagram of a fluid analysis module suitable for use in the borehole tool of FIG. 1.

FIG. 2 illustrates an embodiment of the fluid analysis module 25 of FIG. 1 (labeled 25'), including a probe 202 having a port 204 to admit formation fluid therein. A hydraulic extending mechanism 206 may be driven by a hydraulic system 220 to extend the probe 202 to sealingly engage the formation 14. In alternative implementations, more than one probe can be used or inflatable packers can replace the probe(s) and function to establish fluid connections with the formation and collect fluid samples. The fluid analysis module 25' includes a flowline 207 that carries formation fluid from the port 204 through a fluid analyzer 208. A pump 228 is fluidly coupled to the flowline 207 and is controlled to draw formation fluid into the flowline 207 and possibly to supply formation fluid to the fluid collecting chambers 22 and 23 (FIG. 1) via valve 229 and flowpath 231.

The probe 202 can be realized by the Quicksilver Probe available from Schlumberger Technology Corporation of Sugar Land, Tex., USA. The Quicksilver Probe divides the fluid flow from the reservoir into two concentric zones, a central zone isolated from a guard zone about the perimeter of the central zone. The two zones are connected to separate flowlines with independent pumps. The pumps can be run at different rates to exploit filtrate/fluid viscosity contrast and permeability anistrotropy of the reservoir. Higher intake velocity in the guard zone directs contaminated fluid into the guard zone flowline, while clean fluid is drawn into the central zone. Fluid analyzers analyze the fluid in each flowline to determine the composition of the fluid in the respective flowlines. The pump rates can be adjusted based on such compositional analysis to achieve and maintain desired fluid contamination levels. The operation of the Quicksilver Probe efficiently separates contaminated fluid from cleaner fluid early in the fluid extraction process, which results in obtaining clean fluid in much less time compared to traditional formation testing tools.

In one embodiment, the fluid analyzer 208 includes a light source that directs light to a sapphire prism disposed adjacent the flowline. The reflection of such light is analyzed by a gas refractometer and dual fluoroscene detectors. The gas refractometer qualitatively identifies the fluid phase in the flowline. At the selected angle of incidence of the emitted light, the reflection coefficient is much larger when gas is in contact with the window than when oil or water is in contact with the window. The dual fluoroscene detectors detect free gas bubbles and retrograde liquid dropout to accurately detect single phase fluid flow in the flowline 207. Fluid type is also identified. The resulting phase information can be used to define the difference between retrograde condensates and volatile oils, which can have similar gas-oil ratios (GORs) and live oil densities. It can also be used to monitor phase separation in real time and ensure single phase sampling.

The fluid analyzer 208 may also include dual spectrometers—a filter array spectrometer and a grating type spectrometer. The filter array spectrometer of the analyzer 208 includes a broadband light source (such as a halogen lamp) providing broadband light that passes along optical guides and through an optical chamber in the flowline to an array of optical density detectors that are designed to detect narrow frequency bands (commonly referred to as channels) in the visible and near-infrared spectra as described in U.S. Pat. No. 4,994,671, herein incorporated by reference in its entirety. These channels may include a subset of channels that detect water absorption peaks (which are used to characterize water content in the fluid) and a dedicated channel corresponding to the absorption peak of carbon dioxide ($CO_2$) with dual channels above and below this dedicated channel that subtract out the overlapping spectrum of hydrocarbon and small amounts of water (which are used to characterize $CO_2$ content in the fluid). The filter array spectrometer also employs optical filters that provide for identification of the color (also referred to as "optical density" or "OD") of the fluid in the flowline. Such color measurements support fluid identification, determination of asphaltene content, and pH measurement. More specifically, pH is measured by injecting an analytical reagent (commonly referred to as a pH dye) into the formation fluid that has been drawn into the flowline 207. The pH of the formation fluid is calculated from optical density measurements of the dyed formation fluid at predetermined wavelengths provided by the filter array spectrometer. Details of analytical reagents and corresponding pH measurements are set forth in U.S. Pat. No. 7,339,160; U.S. Pat. No. 7,427,504; U.S. Pat. No. 7,432,109; U.S. Patent Application Publication US 2009/0047181; and U.S. Patent Application Publication US 2009/0084175; each of which is incorporated herein by reference in its entirety. Mud filtrates or other solid materials generate noise in the channels of the filter array spectrometer. Scattering caused by these particles is independent of wavelength. In one embodiment, the effect of such scattering can be removed by subtracting a nearby channel.

The grating type spectrometer of the fluid analyzer 208 is designed to detect channels in the near-infrared spectra (between 1600 and 1800 nm) where reservoir fluid has absorption characteristics that reflect molecular structure.

The fluid analyzer 208 may also include a pressure sensor for measuring pressure of the formation fluid in the flowline 207, a temperature sensor for measuring temperature of the formation fluid in the flowline 207, a density sensor for measuring live fluid density of the fluid in the flowline 207, and a resistivity sensor for measuring resistivity of the fluid in the flowline 207. In one embodiment, the density sensor is realized by a vibrating sensor that oscillates in two perpendicular modes within the fluid. Simple physical models describe the resonance frequency and quality factor of the sensor in relation to live fluid density. Dual mode oscillation is advantageous over other resonant techniques because it minimizes the effects of pressure and temperature on the sensor through common mode rejection. In addition to density, the density sensor can also provide a measurement of live fluid viscosity from the quality factor of oscillation frequency. Note that live fluid viscosity can also be measured by placing a vibrating object in the fluid flow and measuring the increase in line width of any fundamental resonance. This increase in line width is related closely to the viscosity of the fluid. The change in frequency of the vibrating object is closely associated with the mass density of the object. If density is measured independently, then the determination of viscosity is more accurate because the effects of a density change on the mechanical resonances are determined. Generally, the response of the vibrating object is calibrated against known standards.

The fluid analyzer 208 includes an optical sensor for creating an oil-water emulsion from reservoir fluids drawn into the flowline 207 and for performing downhole measurement of the pH of the water phase of the emulsion. An embodiment of such an optical sensor is labeled by arrow 1000 in FIG. 3. The optical sensor 1000 includes a measurement chamber 1006 (of known volume) fluidly coupled to the flowline 207 by a valve 1009. A cylindrical bore 1007 is fluidly coupled to the measurement chamber 1006 by a valve 1010. A piston 1008 is seated within the bore 1007 and can be displaced in a controlled manner by an electromechanical actuation system. The bore 1007 is filled with an aqueous analytical reagent (commonly referred to as a pH dye) that changes color depending on the pH value of the solution to which it is added. Examples of such an analytical reagent are described in U.S. Pat. No. 7,427,504; U.S. Pat. No. 7,432,109; U.S. Patent Application Publication US 2009/0047181; and U.S. Patent Application Publication US 2009/0084175. With the valve 1010 open, the displacement of the piston 1008 in a direction that decreases the volume of the bore 1007 causes the analytical reagent stored in the bore 1007 to be injected into the measurement chamber 1006. A fluid agitator 1011 is positioned in the measurement chamber 1006 for mixing fluids disposed therein. A spectroscopic system comprising of a broadband light source 1012 (e.g., halogen lamp) and a spectrometer 1013 are positioned about the bottom part of the measurement chamber 1006. Light emitted from the light source 1012 is transmitted though the fluid in the bottom part of the measurement chamber 1006 via optical windows 1014. The optical density of the fluid at the bottom of the measurement chamber at one or more predetermined wavelengths is measured by the spectrometer 1013. The pH of the fluid in the bottom part of the measurement chamber 1006 can be calculated from such optical density measurements as described in U.S. Pat. No. 7,339,160; U.S. Pat. No. 7,427,504; U.S. Pat. No. 7,432,109; U.S. Patent Application Publication US 2009/0047181; and U.S. Patent Application Publication US 2009/0084175. The optical sensor 1000 also includes a resistivity sensor 1016 for measuring the resistivity of the fluid in the measurement chamber 1006. The pH of the fluid in the measurement chamber 1006 can be estimated from an empirical correlation to the resistivity of the fluid in the measurement chamber 1006 as is well known in the geochemical arts. The correlation between pH and resistivity can be determined from laboratory analysis over the desired temperature conditions of the measurement using standard buffers of known pH. Dependence of the correlation on pressure may be obtained through experimental calibration if necessary. The optical sensor 1000 also includes a temperature and pressure sensor 1017 for measuring the temperature and pressure of the fluid in the measurement chamber 1006.

Turning back to FIG. 2, the fluid analysis module 25' includes a data processing system 213 that receives and transmits control and data signals to the other components of the module 25' for controlling operations of the module 25'. The data processing system 213 also interfaces to the fluid analyzer 208 for receiving, storing, and processing the measurement data generated therein. In one embodiment, the data processing system 213 processes the measurement data output by the fluid analyzer 208 to derive and store measurements of the fluid samples analyzed in situ by the fluid analyzer 208. The measurements derived and stored by the data processing system 213 include flowline temperature, flowline pressure, concentration (e.g., mole fraction, mass fraction, weight percentage, or mol/unit volume) of carbon dioxide ($CO_2$), pH, resistivity, and concentration (e.g., mole fraction, mass fraction, weight percentage, or mol/unit volume) of hydrogen sulfide ($H_2S$) for the fluid samples. Such measurements can also include additional data measurements, such as live fluid density, live fluid viscosity, concentrations of hydrocarbon components and component groups (i.e., methane ($CH_4$), ethane ($C_2H_6$), the C3-C5 alkane group, the lump of hexane and heavier alkane components (C6+), and asphaltenes), GOR, and possibly other parameters (such as API gravity, oil formation volume factor (Bo), retrograde dew formation, asphaltene precipitation, and gas evolution).

The fluid analysis module 25' also includes a tool bus 214 that communicates data signals and control signals between the data processing system 213 and the control system 18 of FIG. 1. The tool bus 214 can also carry electrical power supply signals generated by a surface-located power source for supply to the fluid analysis module 25', and the module 25' can include a power supply transformer/regulator 215 for transforming the electric power supply signals supplied via the tool bus 214 to appropriate levels suitable for use by the electrical components of the module 25'.

Figure 3:
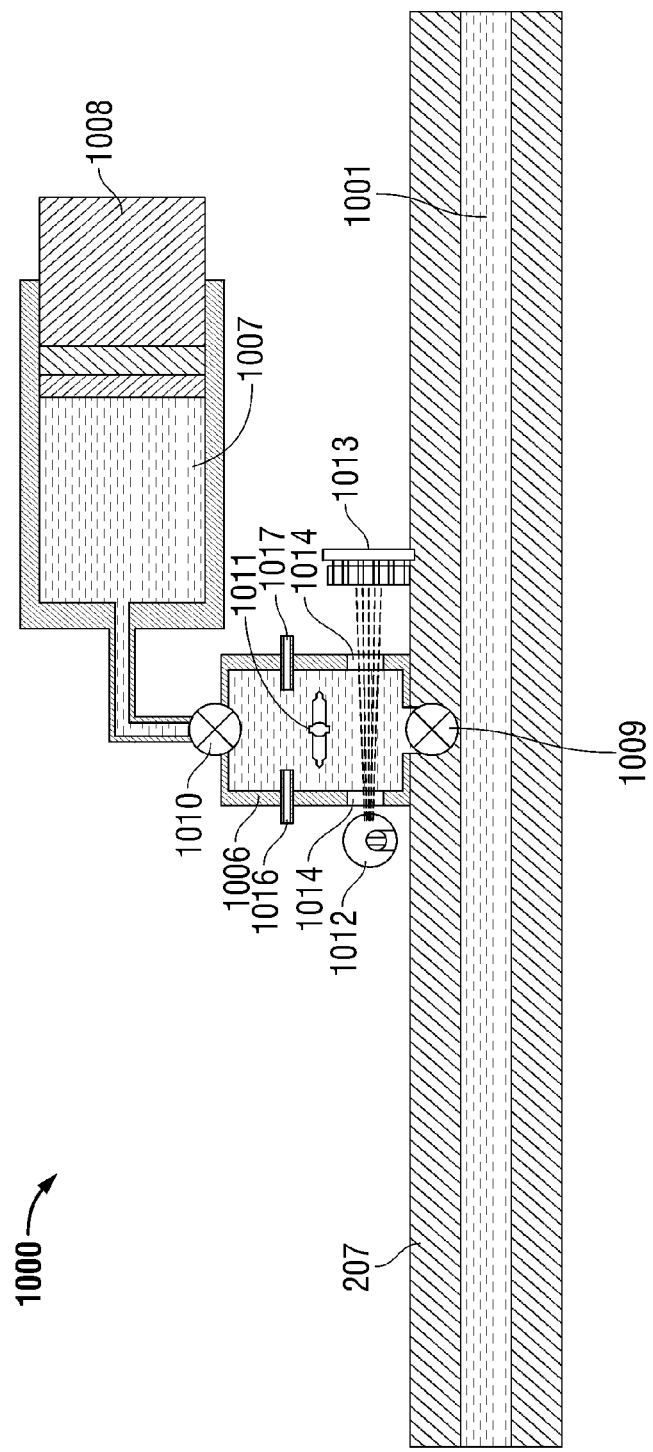
FIG. 3 is a schematic diagram of an optical sensor that is part of the fluid analyzer of FIG. 2; the optical sensor includes a measurement chamber that is used to produce an oil-water emulsion from reservoir fluids and a spectrometer that measures the pH of the water phase of the emulsion.

In one embodiment, the fluid analyzer 208 is based upon adapting the InSitu Fluid Analyzer available from Schlumberger Technology Corporation with the optical sensor 1000 of FIG. 3. In other implementations, the flowline sensors of the fluid analyzer 208 as described above may be replaced or supplemented with other types of suitable measurement sensors (e.g., NMR sensors or capacitance sensors).

Although the components of FIGS. 2 and 3 are shown and described above as being communicatively coupled and arranged in a particular configuration, persons of ordinary skill in the art will appreciate that the components of the fluid analysis module 25' can be communicatively coupled and/or arranged differently than depicted in FIGS. 2 and 3 without departing from the scope of the present disclosure. In addition, the example methods, apparatus, and systems described herein are not limited to a particular conveyance type but, instead, may be implemented in connection with different conveyance types including, for example, coiled tubing, wireline, wired drill pipe, and/or other conveyance means known in the industry.

For measuring hydrogen sulfide concentration in formation fluid, the measurement chamber 1006 of the optical sensor 1000 of FIG. 3 is initially filled with the analytical reagent stored in the bore 1007. A baseline measurement of the temperature and pressure of the analytical reagent as well as the optical density(ies) and resistivity of the analytical reagent at these initial conditions is taken and stored by the data processing system 213. Moreover, formation fluid 1001 has been drawn into the flowline 207 as shown.

Figure 4A:
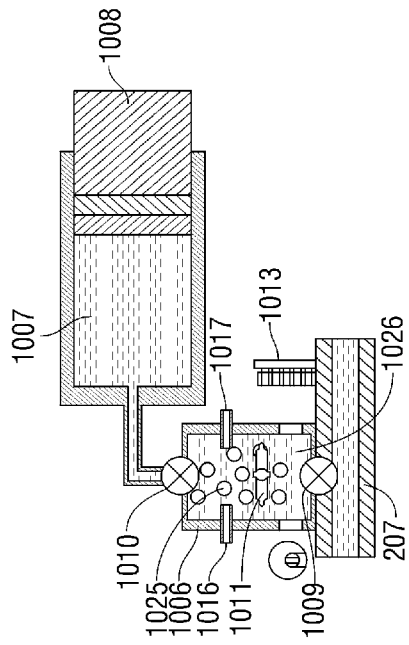
FIGS. 4A-4D are schematic diagrams of the optical sensor of FIG. 3 during different operational stages that produce an oil-water emulsion from reservoir fluids and perform downhole measurement of the pH of the water phase of the emulsion.

The valves 1009 and 1010 are opened and the piston 1008 is drawn back (arrow labeled 1020) as shown in FIG. 4A, thereby increasing the volume of the bore 1007. This piston displacement causes formation fluid to flow from the flowline 207 into the measurement chamber 1006 as shown by arrows 1021.

Figure 4B:
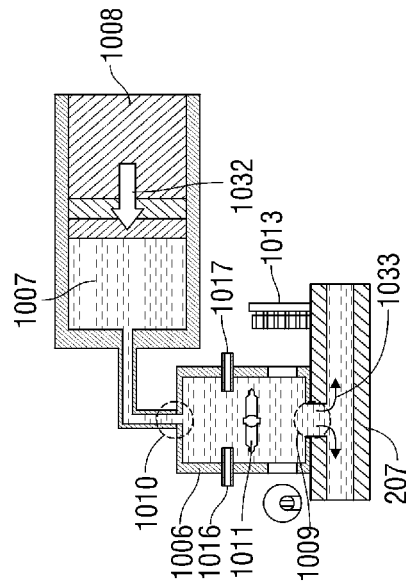

The valves 1009 and 1010 are then closed to isolate the measurement chamber 1006 from the flowline 207 and the cylinder bore 1007 as shown in FIG. 4B. The volume of the formation fluid isolated in the measurement chamber 1006 may be measured from the diameter and displacement of the piston 1008 that caused the inflow of formation fluid into the measurement chamber 1006 (FIG. 4A). This volume can be used to calculate the volume fraction of the formation fluid and the volume fraction of the analytical reagent that are isolated in the measurement chamber 1006. The fluids isolated in the measurement chamber 1006 are then mixed well by the agitator 1011. If the formation fluid is a live crude oil, the mixing of the formation fluid and the aqueous analytical reagent creates an oil-water emulsion (labeled as an oil phase 1025 and a water phase 1026 in FIG. 4B). Some gas components (e.g., carbon dioxide and hydrogen sulfide, if present) of the formation fluid dissolve into the water phase 1026 and reach an equilibrium state. The agitation allows the system to attain equilibrium faster. The concentration of the dissolved gases influences the pH of the water phase 1026, which is reflected in the difference between the optical density of the water phase (as well as the resistivity of the water phase) as compared to the baseline reading of the aqueous analytical reagent.

Figure 4C:
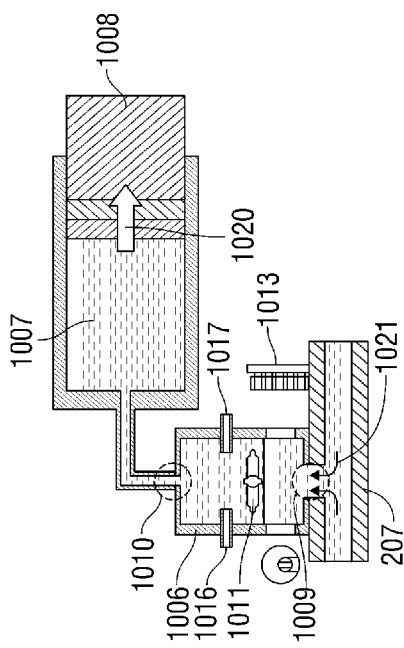
Figure 4D:
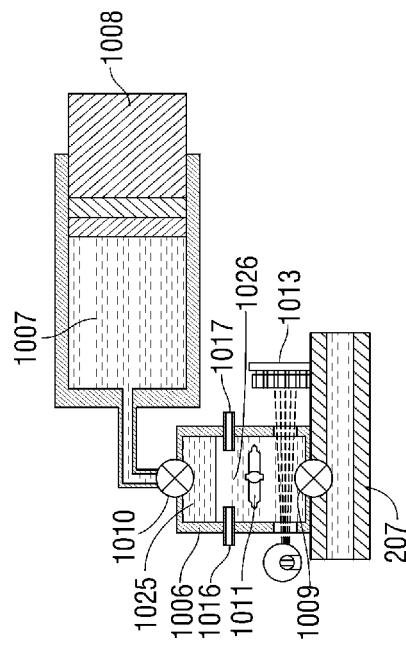

After a period of time (depending on the emulsion stability), the oil phase 1025 of the emulsion separates and floats on top of the water phase 1026, which fills the bottom part of the measurement chamber as shown in FIG. 4C. The optical density of the water phase 1026 can be measured by the spectrometer 1013. The resistivity of the water phase 1026 can be measured by the resistivity sensor 1016. The temperature and pressure of the water phase 1026 can be measured by the temperature and pressure sensor 1017. After these measurements are complete, the valves 1009 and 1010 are opened and the solution is purged from the measurement chamber 1006 into the flowline 207 (as shown by the arrows labeled 1033) by displacement of the piston 1008 (arrow labeled 1032) as shown in FIG. 4D, thereby decreasing the volume of the bore 1007. This piston displacement causes the aqueous analytical reagent to refill the measurement chamber 1006. The valves 1009 and 1010 are then closed to return to the initial conditions of FIG. 3.

Figure 5A:
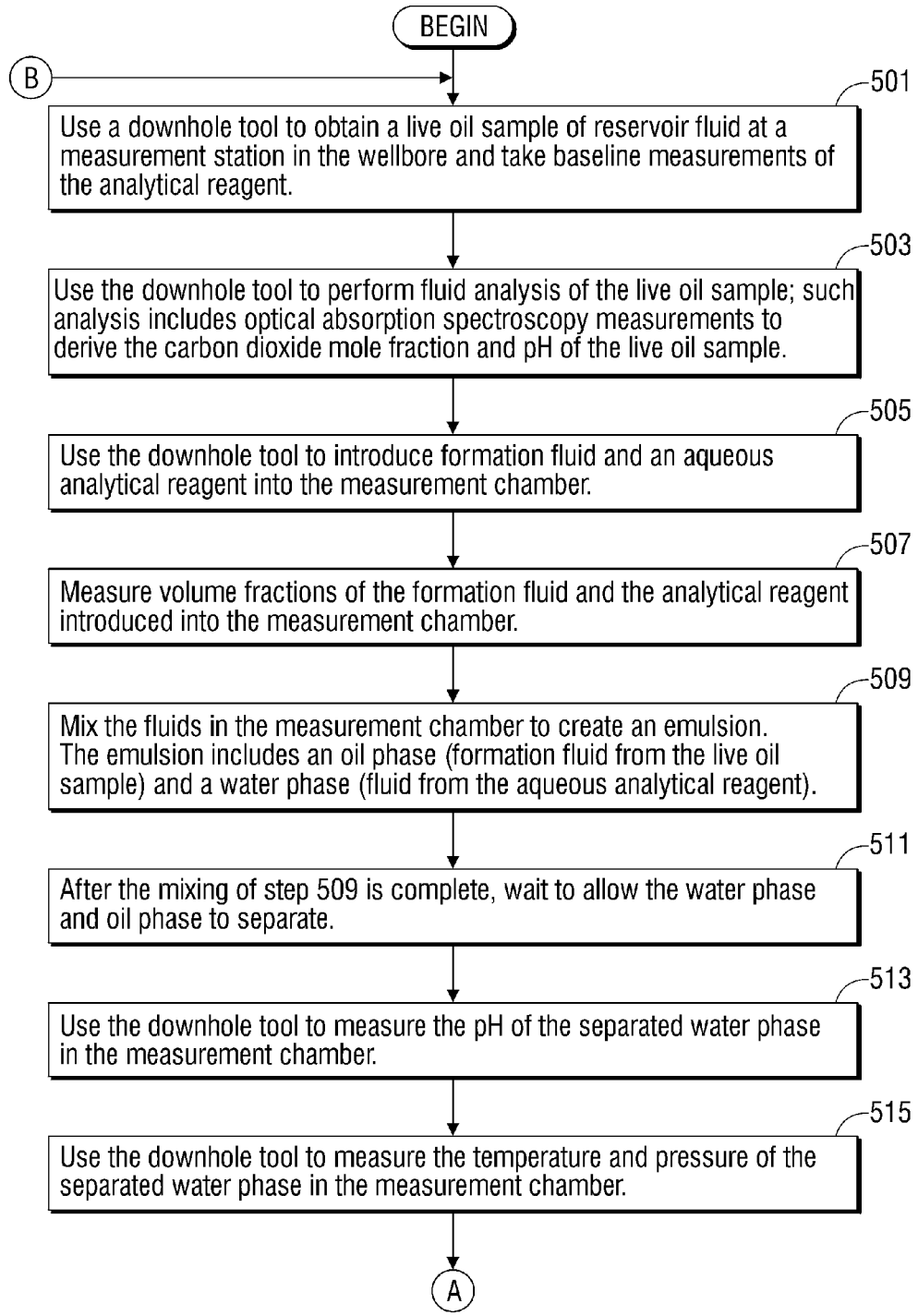
FIG. 5A-5B, collectively, are a flow chart of data analysis operations that include downhole spectroscopy for measuring carbon dioxide concentration of reservoir fluids (and possibly other fluid measurements such as pH and resistivity) in conjunction with measurement of the concentration of hydrogen sulfide in the reservoir fluids based upon a thermodynamic model that relates the pH of the water phase of the oil-water emulsion provided by the optical sensor of FIG. 3 to the dissolution of both carbon dioxide and hydrogen sulfide in the water phase.
Figure 5B:
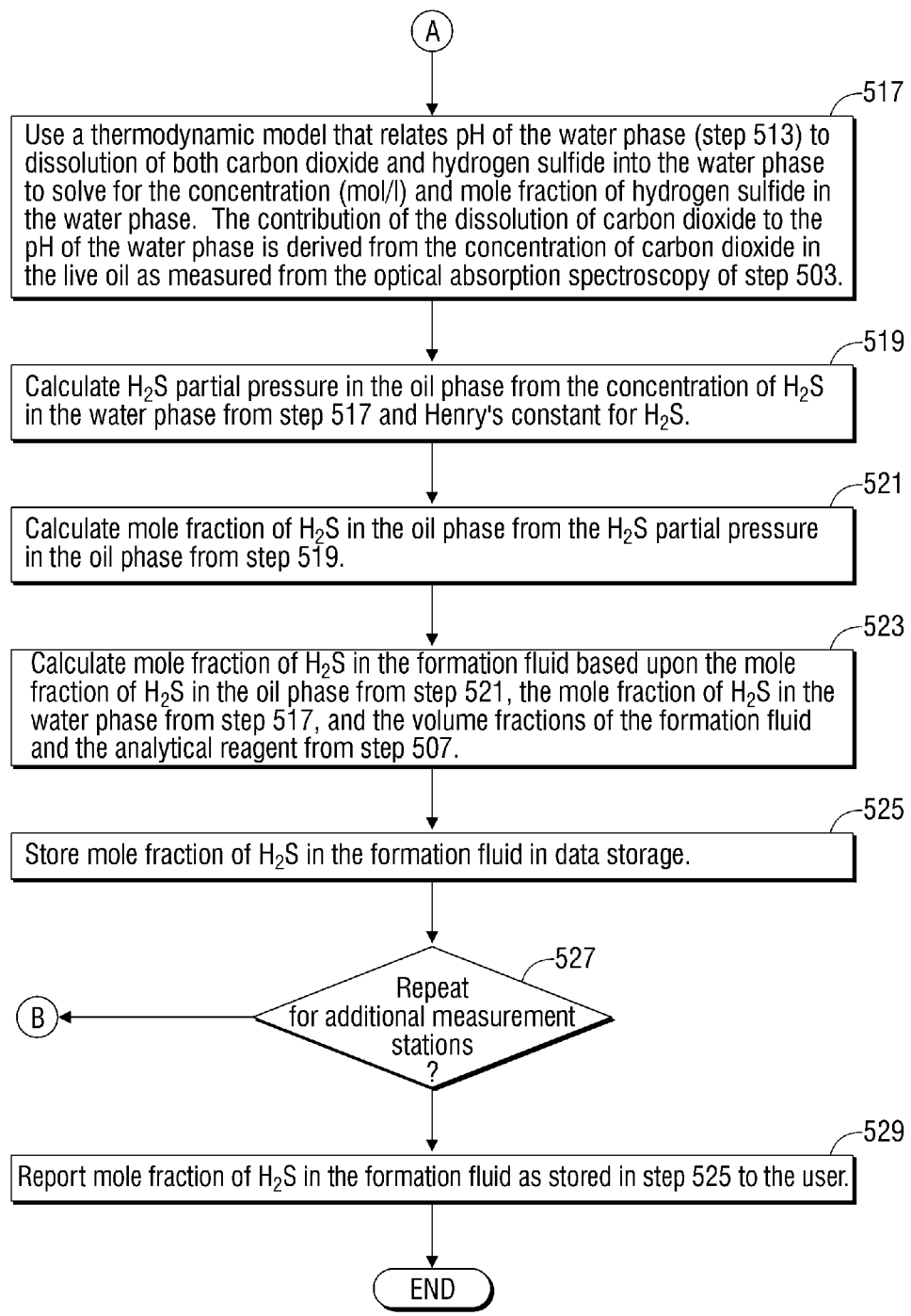

In accordance with the present invention, the downhole measurement system of FIGS. 1-3 can be employed with the methodology of FIGS. 5A-5B to measure the concentration of hydrogen sulfide in a petroleum reservoir of interest based upon downhole fluid analysis of samples of reservoir fluid. As will be appreciated by those skilled in the art, the electrical control system 18 and the fluid analysis module 25 of the borehole tool 10 each include data processing functionality (e.g., one or more microprocessors, associated memory, and other hardware and/or software) that cooperate to implement the invention as described herein. The electrical control system 18 can also be realized by a distributed data processing system wherein data measured by the borehole tool 10 is communicated in real time over a communication link (possibly a satellite link) to a remote location for data analysis as described herein. The data analysis can be carried out on a workstation or other suitable data processing system (such as a computer cluster or computing grid).

The methodology of FIGS. 5A-5B begins in step 501 by using the borehole tool 10 as described above with respect to FIGS. 1-3 to obtain a live oil sample of reservoir fluid at a measurement station in the wellbore. In step 501, baseline measurements of the temperature and pressure of the analytical reagent as well as the optical density(ies) and resistivity of the analytical reagent at these initial conditions is taken by the optical sensor 1000.

In step 503, the downhole tool is used to perform downhole fluid analysis of the live oil sample. Such analysis includes optical absorption spectroscopy measurements to derive the mole fraction of carbon dioxide in the live oil sample as well as the pH of the live oil sample. Details of such optical absorption spectroscopy measurements are set forth above.

In step 505, the optical sensor 1000 of the downhole tool is used to introduce formation fluid 1001 and aqueous analytical reagent into the measurement chamber 1006 as described above and shown in FIG. 4A.

In step 507, the volume fraction of the formation fluid and the volume fraction of the analytical reagent within the measurement chamber 1006 are measured. These volume fractions may be derived from the diameter and displacement of the piston 1008 that caused the inflow of formation fluid into the measurement chamber 1006 (FIG. 4A). The volume fractions can be used to calculate the concentration of hydrogen sulfide in formation fluid from the concentration of hydrogen sulfide in the oil phase and the concentration of hydrogen sulfide in the water phase (step 523).

In step 509, the fluids isolated in the measurement chamber 1006 are mixed by the agitator 1011. If the formation fluid is a live crude oil, the mixing of the formation fluid and the aqueous analytical reagent creates an oil-water emulsion (labeled as an oil phase 1025 and a water phase 1026 in FIG. 4B). Some gas components (e.g., carbon dioxide and hydrogen sulfide, if present) of the formation fluid dissolve into the water phase 1026 and reach an equilibrium state. The agitation of step 509 allows the system to attain equilibrium more rapidly. The concentration of the dissolved gases produces a change in the pH of the water phase 1026, which is reflected in a change in the optical density of the water phase and a change in the resistivity of the water phase.

At step 511, after the mixing of step 509 is complete, the operations wait for a period of time such that the oil phase 1025 of the emulsion separates and floats on top of the water phase 1026, which fills the bottom part of the measurement chamber 1006 as shown in FIG. 4C.

Figure 7:
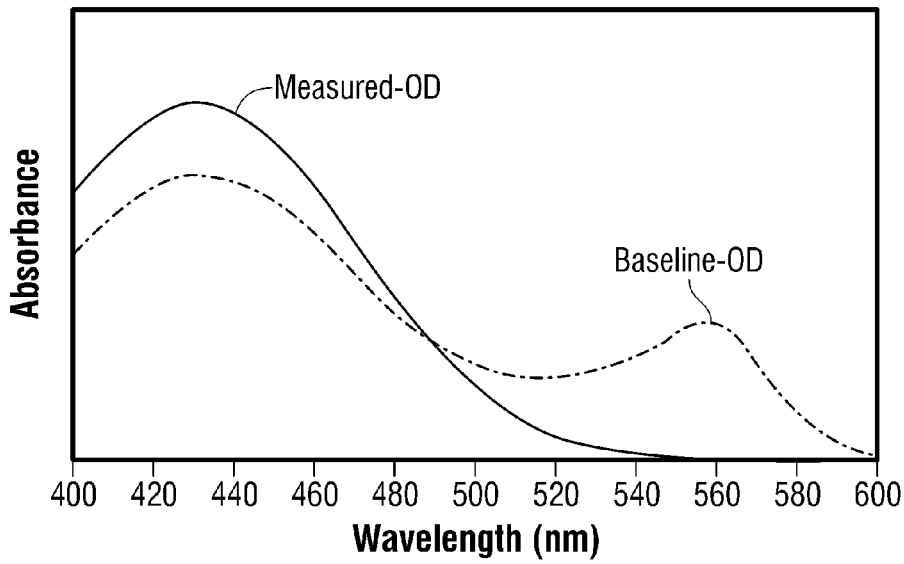
FIG. 7 is a graph that shows the optical absorption spectra of an aqueous reagent solution measured at two different pHs.

In step 513, the optical density of the water phase 1026 is measured by the spectrometer 1013. The resistivity of the water phase 1026 can also be measured by the resistivity sensor 1016. The pH of the water phase 1026 can be calculated from such optical density measurements as described in U.S. Pat. No. 7,339,160; U.S. Pat. No. 7,427,504; U.S. Pat. No. 7,432,109; U.S. Patent Application Publication US 2009/0047181; and U.S. Patent Application Publication US 2009/0084175. FIG. 7 shows the optical absorption spectra of an aqueous reagent solution at two different pHs. The first measurement (labeled "Baseline-OD" is a representative baseline measurement of optical density in step 501. The second measurement (labeled "Measured-OD") is a representative measurement of the optical density of the water phase in step 513. Note that there are large differences in optical absorption spectra at wavelengths at or near 430 nm and 560 nm. In this example, the pH of the water phase can be calculated from optical density measurements of the spectrometer for these two wavelength channels. The pH of the water phase 1026 can also be estimated from an empirical correlation to the measured resistivity of the water phase as is well known in the geochemical arts.

In step 515, the temperature and pressure of the water phase 1026 can be measured by the temperature and pressure sensor 1017.

After the measurements of step 513 and 515 are complete, the valves 1009 and 1010 are opened and the solution is purged from the measurement chamber 1006 into the flowline 207 (as shown by the arrows labeled 1033) by displacement of the piston 1008 (arrow labeled 1032) as shown in FIG. 4D, thereby decreasing the volume of the bore 1007. This piston displacement causes the aqueous analytical reagent to refill the measurement chamber 1006. The valves 1009 and 1010 are then closed to return to the initial conditions of FIG. 3.

Figure 8:
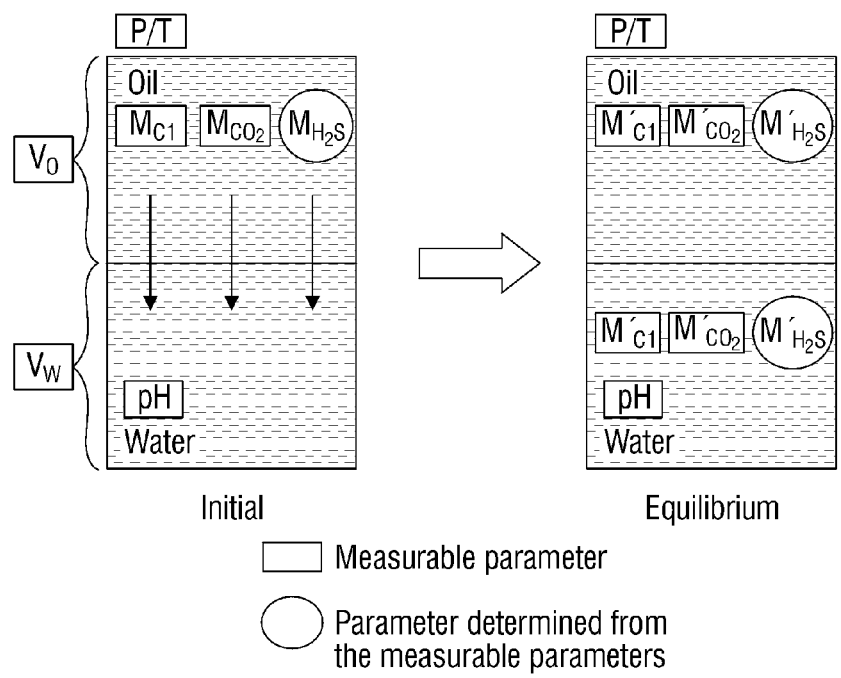
FIG. 8 is a schematic illustration of the separated oil phase and water phase of the oil-water emulsion provided by the optical sensor of FIG. 3 and the parameters that contribute to the pH of the water phase.

In step 517, a thermodynamic model represented by a set of computational equations is used to solve for the concentration (in mol/l and mole fraction) of hydrogen sulfide in the water phase. The computational equations of the thermodynamic model relate the pH of the water phase of the oil-water emulsion provided by the optical sensor of FIG. 3 in step 513 to the concentrations of carbon dioxide components and hydrogen sulfide components that are dissolved in the water phase. The contribution of the dissolved carbon dioxide components to the pH of the water phase is derived from the concentration of the carbon dioxide in the formation fluid (live oil) as measured in step 503. FIG. 8 is a schematic illustration of the oil phase and water phase and the parameters that contribute to the pH of the water phase as represented by the thermodynamic model of step 517. The measured parameters with a subscript C1 refer to methane ($CH_4$). Methane is a major component of gaseous petroleum fluid (natural gas), and can contain significant levels of carbon dioxide and hydrogen sulfide.

In step 519, the partial pressure of hydrogen sulfide in the oil phase of the emulsion is calculated from the concentration of hydrogen sulfide in the water phase from step 517 and Henry's constant for hydrogen sulfide. This step assumes that the oil phase is an ideal solution with thermodynamic properties analogous to those of a mixture of ideal gases. Thus, the enthalpy of the solution (or "enthalpy of mixing") is zero as is the volume change on mixing; the vapor pressure of the solution obeys Raoult's law, and the activity coefficients (which measure deviation from ideality) are equal to one. More specifically, the partial pressure of hydrogen sulfide in the oil phase of the emulsion is related to the concentration of hydrogen sulfide in the water phase and Henry's constant for hydrogen sulfide according to Henry's law, which can be represented as:

$$p = k_H c \tag{1}$$

where
p is the partial pressure of the hydrogen sulfide in the oil phase,
c is the concentration of the hydrogen sulfide in the water phase, and
$k_H$ is Henry's constant for hydrogen sulfide (with the dimensions of pressure divided by concentration).

Henry's constant depends on the solute (hydrogen sulfide), the solvent (water) and temperature (which is measured in step 515). Henry's constant and related coefficients for aqueous hydrocarbons, $CO_2$ and $H_2S$ over a wide range of temperature and pressure can be derived from *Fluid Phase Equilibria* (October 2008), 272 (1-2), pp. 65-74, Vladimir Majer; Josef Sedlbauer; Gaetan Bergin.

In step 521, the mole fraction (dimensionless) of hydrogen sulfide in the oil phase is calculated from the partial pressure of hydrogen sulfide in the oil phase of step 519. This step assumes that the oil phase is an ideal mixture. More specifically, the mole fraction of hydrogen sulfide in the oil phase is related to the partial pressure of the hydrogen sulfide in the oil phase and the total pressure of the oil phase as:

$$x_i = \frac{P_i}{P} \tag{2}$$

where
$x_i$ is the mole fraction of hydrogen sulfide in the oil phase,
$P_i$ is the partial pressure of hydrogen sulfide in the oil phase (from step 519), and
P is the total pressure of the oil phase (which is measured from the output of the temperature and pressure sensor 1017 of the optical sensor 1000 after separation).

In step 523, the mole fraction (dimensionless) of hydrogen sulfide in the formation fluid is calculated based upon the mole fraction of hydrogen sulfide in the oil phase (from step 521), the mole fraction of hydrogen sulfide in the water phase (from step 517), and the volume fractions of the formation fluid and the analytical reagent (from step 507).

More specifically, the mole fraction of hydrogen sulfide in the formation fluid is related to the mole fraction of hydrogen sulfide in the oil phase and the mole fraction of hydrogen sulfide in the water phase as:

$$x_{H2S,sample} = x_{H2S,oil} + \left(x_{H2S,water}\left(\frac{\phi_{water}}{\phi_{oil}}\right)\right) \quad (3)$$

where $x_{H2S,sample}$ is the mole fraction of hydrogen sulfide in the formation fluid, $x_{H2S,oil}$ is the mole fraction of hydrogen sulfide in the oil phase (from step 521), $x_{H2S,water}$ is the mole fraction of hydrogen sulfide in the water phase (from step 517), $\phi_{water}$ is the volume fraction of the reagent calculated in step 507, and $\phi_{oil}$ is the volume fraction of the formation fluid calculated in step 507.

This calculation accounts for the hydrogen sulfide that remains in the oil phase after separation of the oil-water emulsion.

In step 525, the concentration of hydrogen sulfide in the formation fluid is stored in data storage. In step 525, the concentration of hydrogen sulfide in the formation fluid can be represented by the mole fraction calculated in step 523. It can also be represented by different units of measure, such as mole percentage (mole fraction*100), mass fraction (g/g), weight percentage (mass fraction*100), ppm, and (mol/unit volume). Such representations can be derived by translating the mole fraction as calculated in step 523 into the desired unit of measure. For example, the mass fraction (g/g) is related to mole fraction by the relationship:

$$w_i = x_i \frac{M_i}{M} \quad (4)$$

where $w_i$ is the mass fraction of hydrogen sulfide in the formation fluid, $M_i$ is the molar mass of hydrogen sulfide in the formation fluid phase, which is known as 34.08 g/mol, and M is the average molar mass of the formation fluid, which can be estimated from the bulk density of the live oil sample density and the volume of the live oil sample introduced into the measurement chamber.

In step 527, the operations of steps 501-525 can be repeated for additional measurement stations in order to measure hydrogen sulfide at multiple locations (e.g., depths) in the reservoir of interest. Such operations can also be repeated for reservoir fluid samples collected from a given measurement station if desired.

In step 529, the measurement of hydrogen sulfide concentration (in units of mole fraction, mole percentage, mass fraction, weight percentage, ppm, or mol/unit volume) in the formation fluid as stored in step 525 is reported to the user. The reporting can be integrated as part of a well log or other suitable graph that is displayed for evaluation of the fluid properties of the reservoir of interest.

In one embodiment, the thermodynamic model of step 517 treats the water phase as an ideal solution. These assumptions allow the individual contribution of both carbon dioxide and hydrogen sulfide to the ion concentration in the water phase to be calculated directly utilizing equilibrium constants, which are readily available as a function of temperature. In this case, the thermodynamic model involves the following reactions and corresponding equilibrium constants as provided in Table I below.

TABLE 1

| Reaction | Equilibrium Constant | Contribution |
|---|---|---|
| $2H_2O \leftrightarrow OH^- + H_3O^+$ | $K_w = [OH^-][H_3O^+]$ | ionization of water |
| $CO_2 + 2H_2O \leftrightarrow HCO_3^- + H_3O^+$ | $K_1 = \frac{[HCO_3^-][H_3O^+]}{[CO_2]}$ | dissociation of $CO_2$ |
| $HCO_3^- + H_2O \leftrightarrow CO_3^{2-} + H_3O^+$ | $K_2 = \frac{[CO_3^{2-}][H_3O^+]}{[HCO_3^-]}$ | dissociation of bicarbonate |
| $H_2S + H_2O \leftrightarrow HS^- + H_3O^+$ | $K_3 = \frac{[HS^-][H_3O^+]}{[H_2S]}$ | dissociation of $H_2S$ |
| $HS^- + H_2O \leftrightarrow S^{2-} + H_3O^+$ | $K_4 = \frac{[S^{2-}][H_3O^+]}{[HS^-]}$ | dissociation of bicarbonate |

The equilibrium constants $K_w \ldots K_4$ based on mole fraction scales can be provided by the formulation of $\ln K_i = C1_i + C2_i/T + C3_i \ln T + C4_i T$, where the corresponding parameters for different equilibrium constants $K_w \ldots K_4$ are given in Table II below:

TABLE II

| $K_i$ | $C1_i$ | $C2_i$ | $C3_i$ | $C4_i$ | Temperature Range (C.) |
|---|---|---|---|---|---|
| $K_w$ | 132.899 | −13,445.9 | −22.4773 | 0.0 | 0-225 |
| $K_1$ | 231.465 | −12,092.10 | −36.7816 | 0.0 | 0-225 |
| $K_2$ | 216.049 | −12,431.70 | −35.4819 | 0.0 | 0-225 |
| $K_3$ | 214.582 | −12,995.4 | −33.5471 | 0.0 | 0-150 |
| $K_4$ | −32.0 | −3338.0 | 0.0 | 0.0 | 14-70 |

Figure 6:
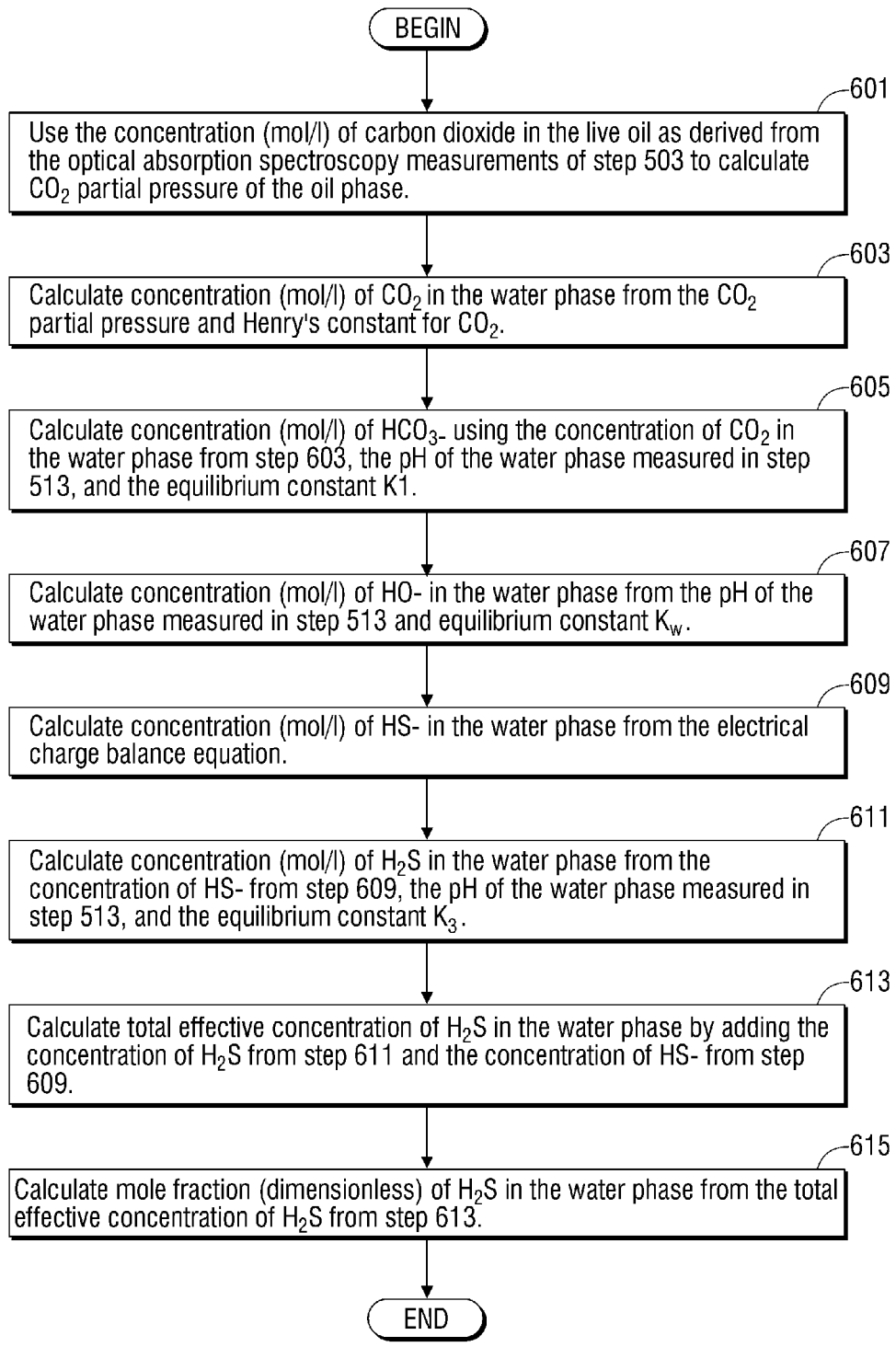
FIG. 6 is a flow chart illustrating calculations of a thermodynamic model that relates the pH of the water phase of the oil-water emulsion provided by the optical sensor of FIG. 3 to the dissolution of both carbon dioxide and hydrogen sulfide in the water phase.

These equilibrium constants can be used to relate the pH of the water phase of the oil-water emulsion provided by the optical sensor of FIG. 3 to the dissolution of both carbon dioxide and hydrogen sulfide in the water phase as provided by the calculations of FIG. 6. These calculations assume that the secondary dissociations of carbon dioxide and hydrogen sulfide to bicarbonate (i.e., the reactions related to $K_2$ and $K_4$) are negligible.

In step 601, the concentration (mol/l) of carbon dioxide in the live oil sample (the oil phase) as derived from the optical absorption spectroscopy measurements of step 503 is used to calculate carbon dioxide partial pressure of the oil phase. This step assumes that the oil phase is an ideal mixture. More specifically, the partial pressure of carbon dioxide in the oil phase is related to the concentration of carbon dioxide in the oil phase and the total pressure of the oil phase as:

$$P_i = x_i P \quad (5)$$

where $P_i$ is the partial pressure of carbon dioxide in the oil phase, and $x_i$ is the mole fraction of carbon dioxide in the oil phase (as derived from the optical absorption spectroscopy measurements of step 503), and P is the total pressure of the oil phase (which is output of the temperature and pressure sensor 1017 of the optical sensor 1000 after separation.

In step 603, the concentration (mol/l) of carbon dioxide in the water phase is calculated from the carbon dioxide partial pressure of step 601 and Henry's constant for carbon dioxide. This step assumes that the oil-water emulsion is an ideal mixture. More specifically, the concentration of carbon dioxide in the water phase is related to the partial pressure of carbon dioxide in the oil phase and Henry's constant for carbon dioxide according to Henry's law, which can be represented as:

$$c = \frac{p}{k_H} \quad (6)$$

where
- c is the concentration of the carbon dioxide in the water phase,
- p is the partial pressure of the carbon dioxide in the oil phase (step 601), and
- $k_H$ is Henry's constant for carbon dioxide (with the dimensions of pressure divided by concentration).

Henry's constant depends on the solute (carbon dioxide), the solvent (water) and temperature (which is measured in step 515). Henry's constant and related coefficients for aqueous hydrocarbons, $CO_2$ and $H_2S$ over a wide range of temperature and pressure can be derived from *Fluid Phase Equilibria* (October 2008), 272 (1-2), pp. 65-74, Vladimir Majer; Josef Sedlbauer; Gaetan Bergin.

In step 605, the concentration (mol/l) of the $HCO_3$— anion in the water phase is calculated from the carbon dioxide concentration in the water phase from step 603, the pH of the water phase as measured in step 513, and the equilibrium constant $K_1$. More specifically, the concentration of the $HCO_3$— anion in the water phase is related to the carbon dioxide concentration in the water phase from step 603, the pH of the water phase as measured in step 513, and the equilibrium constant $K_1$ by:

$$[HCO_3^-] = \frac{K_1[CO_2]}{10^{-pH}} \quad (7)$$

where
- $[HCO_3^-]$ is the concentration of the $HCO_3$— anion in the water phase,
- $[CO_2]$ is the concentration of carbon dioxide in the water phase (from step 603),
- pH is the pH of the water phase (measured in step 513), and
- $K_1$ is the equilibrium constant for the first dissociation of the carbon dioxide.

The value of $K_1$ can be calculated from the parameters of Table II for the temperature measured in step 515.

In step 607, the concentration (mol/l) of the HO— anion in the water phase is calculated from the pH of the water phase as measured in step 513 and the equilibrium constant $K_w$. More specifically, the concentration of the HO— anion in the water phase is related to the pH of the water phase as measured in step 513 and the equilibrium constant $K_w$ by:

$$[OH^-] = \frac{K_w}{10^{-pH}} \quad (8)$$

where

- $[OH^-]$ is the concentration of the OH— anion in the water phase,
- pH is the pH of the water phase (measured in step 513), and
- $K_w$ is the equilibrium constant for the ionization of water.

This relation assumes that the concentration of dissolved solutes is not very high. The value of $K_w$ can be calculated from the parameters of Table II for the temperature measured in step 515.

In step 609, the concentration (mol/l) of the HS— anion in the water phase is calculated from a charge balance equation as follows:

$$[HS^-] = [H_3O^+] - [HCO_3^-] - [OH^-] \quad (9)$$

where
- $[HS^-]$ is the concentration (mol/l) of the HS— anion in the water phase,
- $[H_3O^+]$ is the concentration (mol/l) of the $H_3O^+$ cation in the water phase, which can be calculated from the pH of the water phase measured in step 513 ($[H_3O^+]=10^{-pH}$),
- $[HCO_3^-]$ is the concentration (mol/l) of the $HCO_3$— anion in the water phase (from step 605), and
- $[OH^-]$ is the concentration (mol/l) of the $OH^-$ anion in the water phase (from step 607).

In step 611, the concentration (mol/l) of $H_2S$ in the water phase is calculated from the concentration of the HS— anion in the water phase from step 609, the pH of the water phase as measured in step 513, and the equilibrium constant $K_3$. More specifically, the concentration of $H_2S$ in the water phase is related to the concentration of the HS— anion in the water phase from step 603, the pH of the water phase as measured in step 513, and the equilibrium constant $K_3$ by:

$$[H_2S] = \frac{[HS^-] \, 10^{-pH}}{K_3} \quad (10)$$

where
- $[H_2S]$ is the concentration of $H_2S$ in the water phase,
- $[HS^-]$ is the concentration of the HS— anion in the water phase (from step 609),
- pH is the pH of the water phase (measured in step 513), and
- $K_3$ is the equilibrium constant for the first dissociation of the hydrogen sulfide.

The value of $K_3$ can be calculated from the parameters of Table II for the temperature measured in step 515.

In step 613, the total effective concentration (mol/l) of $H_2S$ in the water phase is calculated by adding the concentration of hydrogen sulfide in the water phase as calculated in step 611 to the concentration of the HS— anion in the water phase as calculated in step 609 as:

$$[H_2S_{overall}] = [H_2S] + [HS^-] \quad (11)$$

where
- $[H_2S_{overall}]$ is the total effective concentration (mol/l) of $H_2S$ in the water phase,
- $[H_2S]$ is the concentration of hydrogen sulfide in the water phase (from step 611),
- $[HS^-]$ is the concentration of the HS— anion in the water phase (from step 609).

In step 615, the mole fraction (dimensionless) of hydrogen sulfide in the water phase is calculated from the total effective concentration (mol/l) of $H_2S$ in the water phase. More particularly, the mole fraction of hydrogen sulfide in the water phase is calculated as:

$$[H_2S_{overall}]/([CO_2]+[HCO_3^-]+[H^+]+[OH^-]+[H_2O]+ \\ [H_2S_{overall}]) \quad (12)$$

$$\text{or approximated by } [H_2S_{overall}]/[H_2O] \quad (13)$$

where
- $[H_2S_{overall}]$ is the total effective concentration (mol/l) of $H_2S$ in the water phase,
- $[CO_2]$ is the concentration of carbon dioxide in the water phase (from step 603),
- $[HCO_3^-]$ is the concentration (mol/l) of the $HCO_3-$ anion in the water phase (from step 605),
- $[H^+]$ is $10^{-pH}$,
- $[OH^-]$ is the concentration (mol/l) of the $OH^-$ anion in the water phase (from step 607), and
- $[H_2O]$ is the concentration of water existing as molecules rather than ions.

While the calculations of the thermodynamic model of FIG. 6 treat the water phase as an ideal solution, alternative thermodynamic models can be used that take into account the non-ideality of the water phase by providing an accurate estimation of activity coefficient. Several models may be suitable for this calculation. For example, one of such models is the Electrolyte-NRTL model developed by Chen et al., which is described in a series of papers including Chen et al., "A Local Composition Model for the Excess Gibbs Energy of Aqueous-Electrolyte Systems," *AICHE Journal*, Vol. 32, No. 3, March 1986, pp. 444-454; Chen et al., "Local Composition Model for the Excess Gibbs Energy of Aqueous-Electrolyte Systems. 1: Single Solvent, Single Completely Dissociated Electrolyte Systems," *AICHE Journal*, Vol. 28, No. 4, 1982, pp. 588-596; and Chen et al., "Extension and Application of the Pitzer Equation for Vapor-Liquid-Equilibrium of Aqueous-Electrolyte Systems with Molecular Solutes," *AICHE Journal*, Vol. 25, No. 5, 1979, pp. 820-831, incorporated herein by reference in their entireties. This model is a generalized excess Gibbs energy model that accounts for molecular/ionic interactions between all the liquid phase species. The model postulates the excess Gibbs energy to be the sum of two contributions, one related to the short range or local interactions between all the species and the other related to the long range electrostatic interactions between ions. The Non-Random Two Liquids (NRTL) theory is adopted to account for the local contribution, while the Pitzer Debye Huckel formula is used to represent the long range interaction contribution. Given the activity coefficients, the concentration of different ions would be calculated in a similar manner as those in the initial estimation and therefore the rigorous relative pH contributions would be obtained.

The hydrogen sulfide measurements as described above can be carried out in conjunction with equation of state (EOS) modeling of the thermodynamic behavior of the fluid (and other predictive property modeling schemes) in order to characterize the reservoir fluid at different locations within the reservoir. With the reservoir fluid characterized with respect to its thermodynamic behavior, fluid production parameters, transport properties, and other commercially useful indicators of the reservoir can be computed. For example, the EOS modeling can provide the phase envelope that can be used to interactively vary the rate at which samples are collected in order to avoid entering the two phase region. In another example, the EOS can provide properties useful in assessing production methodologies for the particular reserve. Such properties can include density, viscosity, and volume of gas formed from a liquid after expansion to a specified temperature and pressure. The characterization of the fluid sample with respect to its thermodynamic model can also be used as a benchmark to determine the validity of the obtained sample, whether to retain the sample, and/or whether to obtain another sample at the location of interest. More particularly, based on the thermodynamic model and information regarding formation pressures, sampling pressures, and formation temperatures, if it is determined that the fluid sample was obtained near or below the bubble line of the sample, a decision may be made to jettison the sample and/or to obtain a sample at a slower rate (i.e., a smaller pressure drop) so that gas will not evolve out of the sample. Alternatively, because knowledge of the exact dew point of a retrograde gas condensate in a formation is desirable, a decision may be made, when conditions allow, to vary the pressure drawdown in an attempt to observe the liquid condensation and thus establish the actual saturation pressure.

Advantageously, the downhole sensing method and apparatus of the present invention does not require transportation of reservoir fluids to a surface laboratory for measuring hydrogen sulfide concentration, and thus can be carried out by a downhole fluid analysis tool at multiple measurement stations during one trip of the tool within the wellbore. It can also be integrated into stationary wellbore sensors in order to monitor the concentration of hydrogen sulfide in reservoir fluids.

There have been described and illustrated herein several embodiments of a method and apparatus for characterizing hydrogen sulfide in petroleum fluid. While particular embodiments of the invention have been described, it is not intended that the invention be limited thereto, as it is intended that the invention be as broad in scope as the art will allow and that the specification be read likewise. Thus, while particular downhole tools and analysis techniques have been disclosed for characterizing properties of the reservoir fluid and surrounding formation, it will be appreciated that other tools and analysis techniques could be used as well. Moreover, the methodology described herein is not limited to stations in the same wellbore. For example, measurements from samples from different wells can be analyzed as described herein for testing for lateral connectivity. In addition, the thermodynamic models as described herein can be modified. It will therefore be appreciated by those skilled in the art that yet other modifications could be made to the provided invention without deviating from its scope as claimed.

What is claimed is:

1. A method of characterizing hydrogen sulfide in petroleum fluid of a reservoir traversed by a subterranean wellbore, the method comprising:
   (a) locating a downhole apparatus within the subterranean wellbore, the downhole apparatus including a fluid admitting assembly for acquiring a live oil sample of the petroleum fluid of the reservoir and a fluid analyzer for performing downhole fluid analysis of the live oil sample, wherein the fluid analyzer comprises a storage chamber fluidly coupled to a measurement chamber, wherein the storage chamber stores an analytical reagent that can be supplied to the measurement chamber, and a flowline that holds the live oil sample, wherein the flowline is fluidly coupled to the measurement chamber;
   (b) using the fluid admitting assembly to acquire a live oil sample of the petroleum fluid of the reservoir;
   (c) using the fluid analyzer to perform downhole fluid analysis of the live oil sample to determine properties of the live oil sample, the properties including concentration of carbon dioxide in the live oil sample;

(d) producing an oil-water emulsion in the measurement chamber by mixing the fluid of the live oil sample and the analytical reagent using a fluid agitator positioned in the measurement chamber, wherein the oil-water emulsion includes fluid of the live oil sample and the analytical reagent supplied from the storage chamber, wherein the analytical reagent changes color due to changes of pH that arise from chemical reactions between components of the live oil sample and the analytical reagent in the measurement chamber;

(e) allowing for separation of the oil-water emulsion into an oil phase and a water phase, the oil phase including the fluid of the live oil sample, and the water phase including the analytical reagent;

(f) providing an optical sensor that measures optical density of the water phase at one or more determined wavelengths, wherein the optical sensor is disposed about a portion of the measurement chamber that holds the water phase, and wherein a bottom portion of the measurement chamber holds the water phase;

(g) determining via a data processing system a measurement of pH of the water phase based upon the optical density measured in (f);

(h) selecting via the data processing system a thermodynamic model that includes terms for pH of the water phase, concentrations of carbon dioxide components, and hydrogen sulfide components that are dissolved in the water phase, wherein contribution of the carbon dioxide components to the pH of the water phase is determined from the concentration of carbon dioxide in the live oil sample as measured in (c); and (i) calculating via the data processing system a concentration of hydrogen sulfide in the live oil sample using the measurement of pH of the water phase of (g), the concentration of carbon dioxide in the live oil sample of (c), and the selected thermodynamic model.

2. A method according to claim 1, wherein:
the concentration of hydrogen sulfide in the live oil sample is derived from partial pressure of hydrogen sulfide in the oil phase and the total pressure of the oil phase, and wherein the partial pressure of hydrogen sulfide in the oil phase is calculated from the concentration of hydrogen sulfide in the water phase and Henry's constant for hydrogen sulfide.

3. A method according to claim 1, wherein:
the thermodynamic model utilizes equilibrium constants to calculate the contribution of carbon dioxide components and hydrogen sulfide components to ion concentration in the water phase, wherein the equilibrium constants are defined as a function of temperature.

4. A method according to claim 1, wherein:
the concentration of hydrogen sulfide in the live oil sample is represented by a unit of measure selected from the group consisting of: mole fraction, mole percentage, mass fraction, weight percentage, ppm, and mol/unit volume.

5. A method according to claim 1, further comprising measuring temperature and pressure of the water phase for use in calculations of the thermodynamic model.

6. A method according to claim 1, wherein the oil phase and water phase of the oil-water emulsion separate in the measurement chamber with the water phase filling the bottom portion of the measurement chamber.

7. A method according to claim 1, wherein:
a first valve is fluidly coupled between the measurement chamber and the flowline, and a second valve is fluidly coupled between the measurement chamber and the storage chamber, wherein the first and second valves are operated to isolate a volume of the measurement chamber for producing the oil-water emulsion in the measurement chamber.

8. A method according to claim 1, wherein the storage chamber employs a displaceable piston operable to inject the analytical reagent from the storage chamber into the measurement chamber.

9. A method according to claim 8, wherein the displaceable piston is further operable to draw fluids from the live oil sample into the measurement chamber.

10. A method according to claim 1, wherein the fluid analyzer includes a spectrometer for measuring optical density of the live oil sample at a plurality of predetermined wavelengths, and for determining the concentration of carbon dioxide in the live oil sample based upon the optical density of the live oil sample at one or more of the predetermined wavelengths.

11. A method according to claim 1, wherein the downhole apparatus is a downhole tool positionable at multiple stations with the subterranean wellbore.

12. A method according to claim 1, wherein the downhole apparatus is a sensor disposed at a fixed position within the subterranean wellbore.

13. A method of characterizing hydrogen sulfide in petroleum fluid of a reservoir, the method comprising:
(a) acquiring a live oil sample of the petroleum fluid of the reservoir;
(b) using a fluid analyzer to perform fluid analysis of the live oil sample to determine properties of the live oil sample, the properties including concentration of carbon dioxide in the live oil sample, wherein the fluid analyzer comprises a storage chamber fluidly coupled to a measurement chamber, and a flowline that holds the live oil sample;
(c) producing an oil-water emulsion in the measurement chamber fluidly coupled to the flowline and the storage chamber that stores an analytical reagent that can be supplied to the measurement chamber by mixing the fluid of the live oil sample and the analytical reagent using a fluid agitator positioned in the measurement chamber, wherein the oil-water emulsion includes fluid of the live oil sample and the analytical reagent supplied from the storage chamber, wherein the analytical reagent changes color due to changes of pH that arise from chemical reactions between components of the live oil sample and the analytical reagent in the measurement chamber;
(d) allowing for separation of the oil-water emulsion into an oil phase and a water phase, the oil phase including the fluid of the live oil sample, and the water phase including the analytical reagent;
(e) providing an optical sensor that measures optical density of the water phase at one or more determined wavelengths, wherein the optical sensor is disposed about a portion of the measurement chamber that holds the water phase, and wherein a bottom portion of the measurement chamber holds the water phase;
(f) determining via a data processing system a measurement of pH of the water phase based upon the optical density measured in (e);
(g) selecting via the data processing system a thermodynamic model that includes terms for pH of the water phase, concentrations of carbon dioxide components, and hydrogen sulfide components that are dissolved in the water phase, wherein contribution of the carbon dioxide components to the pH of the water phase is determined from the concentration of carbon dioxide in the live oil sample as measured in (b); and (h) calculating via the data processing system a concentration of hydrogen sulfide in the live oil sample using the measurement of pH of the water phase of (f), the concentration of carbon dioxide in the live oil sample of (b), and the selected thermodynamic model.

* * * * *